(12) United States Patent
Erickson

(10) Patent No.: US 6,380,177 B1
(45) Date of Patent: Apr. 30, 2002

(54) LPA ANALOGS AS AGONISTS OF THE EDG2 LPA RECEPTOR

(75) Inventor: James R. Erickson, El Cerrito, CA (US)

(73) Assignee: Atairgin Technologies, Inc., Irvine, CA (US)

(*) Notice: Subject to any disclaimer, the term of this patent is extended or adjusted under 35 U.S.C. 154(b) by 0 days.

(21) Appl. No.: 09/602,235

(22) Filed: Jun. 23, 2000

Related U.S. Application Data (60) Provisional application No. 60/141,078, filed on Jun. 25, 1999.

(51) Int. Cl.[7] .............................................. A01N 57/18
(52) U.S. Cl. ......................... 514/141; 514/143; 554/78
(58) Field of Search ............................. 584/79, 81, 78; 532/55; 558/78, 79; 560/129; 514/75, 767, 141, 143

(56) References Cited

U.S. PATENT DOCUMENTS

| 5,480,877 A | 1/1996 | Mosher, Jr. et al. |
| 5,565,439 A | 10/1996 | Piazza et al. |

FOREIGN PATENT DOCUMENTS

| FR | 0 747 047 a1 | 5/1995 | |
| JP | 51076423 | 7/1976 | |
| WO | WO 99/08514 | 8/1997 | |
| WO | WO 99/19513 | 10/1997 | |
| WO | WO 99/47101 | 3/1998 | |
| WO | 98/41213 | * 9/1998 | .......... A61K/31/66 |

OTHER PUBLICATIONS

An, S., M.A. Dickens, T. Bleu, O.G. Hallmark and E.J. Goetzl (1997) *Biochem. Biophys. Res. Comm.* 231, 619–622.

An, S., T. Bleu, O.G. Hallmark and E.J. Goetzl (1998) Characterization of a novel subtype of human G protein–coupled receptor for lysophosphatidic acid. *J. Biol. Chem.* 273, 7906–7910.

Erickson, J.R., J.J. Wu, J.G. Goddard, G. Tigyi, K. Kawanishi, L.D. Tomei and M.C. Kiefer (1998) Edg–2/vzg–1 couples to the yeast pheromone response pathway selectively in response to lysophosphatidic acid *J. Biol. Chem.* 273, 1506–1510.

Fischer, D.J., K. Liliom, Z. Guo, N. Nusser, T. Virag, K. Murakami–Murofushi, S. Kobayashi, J.R. Erickson, G. Sun, D.D. Miller and G. Tigyi. (1998) Naturally occurring analogs of lysophosphatidic acid elicit different cellular responses through selective activation of multiple receptor subtypes. *Mol. Pharmacol.* 54:979–988.

Guo, Z., K. Liliom, D.J. Fischer, I.C. Bathurst, L.D. Tomei, M.C. Kiefer and G. Tigyi (1996) Molecular cloning of a high–affinity receptor for the growth factor–like lipid mediator lysophosphatidic acid from *Xenopus* oocytes *Proc. Natl. Acad. Sci. USA* 93, 14367–14372.

(List continued on next page.)

*Primary Examiner*—Deborah D. Carr
(74) *Attorney, Agent, or Firm*—Lyon & Lyon LLP (57) ABSTRACT

Applicant has probed the Edg2 lysophosphatidic acid (LPA) receptor with a series of LPA analogs to determine receptor activation. The present invention is drawn to a series of LPA analogs which function as Edg2 receptor agonists, and methods of using such compounds to activate the Edg2 receptor of the surface of a cell. The compounds of the invention comprise a glycerol backbone with an Sn1 ester-linked saturated or unsaturated alkyl group, substitutions of the hydroxyl group (—OH) at carbon two of the glycerol backbone, and optional replacement of the phosphate di-anion with either a hydroxyl group or a dimethylated phosphate. These LPA analogs may find uses in cancer and neurological disorders.

11 Claims, 5 Drawing Sheets

OTHER PUBLICATIONS

Hecht, J.H., J.A. Weiner, S.R. Post and J. Chun (1996) Ventricular zone gene–1 (vzg–1) encodes a lysophosphatidic acid receptor expressed in neurogenic regions of the developing cerebral cortex *J. Cell Biol.* 135, 1071–1083.

Hopper, D.W., S.P. Ragan, S.B. Hooks, K.R. Lynch and T.L. Macdonald (1999) Structure–activity relationship of lysophosphatidic acid: Conformationally restricted backbone mimetics. *J. Med. Chem.* 42:963–970.

Hooks, S.B., S.P. Ragan, D.W. Hopper, C.W. Honemann, M.E. Durieux, T.L. Macdonald and K.R. Lynch (1998) Characterization of a receptor subtype–selective lysophosphatidic acid mimetic. *Mol. Pharmacol.* 53, 188–194.

Ishii, I., T. Izumi, H. Tsukamoto, H. Umeyama, M. Ui and T. Shimizu (1997) *J. Biol. Chem.* 272, 7846–7845.

Jalink, K, T. Hengeveld, S. Mulder, F.R. Postma, M.–F. Simon, H. Chap, G.A. van der Marel, J.H. van Boom, W.J. van Blitterswijk and W.H. Moolenaar (1995) *Biochem. J.* 307, 609–616.

Lee, M.–J., M. Evans and T. Hla (1996) *J. Biol. Chem.* 271, 11272–11279.

Liliom, K., R. Bittman, B. Swords and G. Tigyi (1996) N–palmitoyl–serine and N–palmitoyl–tyrosine phosphoric acids are selective competitive antagonists of the lysophosphatidic acid receptors. *Mol. Pharmacol.* 50:616–623.

Lynch, K.R., D.W. Hopper, S.J. Carlisle, J.G. Catalano, M. Zhang and T.L. Macdonald (1997) Structure/activity relationships in lysophosphatidic acid: The 2–hydroxyl moiety. *Mol. Pharmacol.* 52, 75–81.

MacLennan, A.J., C.S. Browe, A.A. Gaskin, D.C. Lado and G. Shaw (1994) *Mol. Cell. Neurosci.* 5, 201–209.

Macrae, A.D., R.T. Premont, M. Jaber, A.S. Peterson, R.J. Lefkowtiz (1996) *Mol. Brain Res.* 42, 245–254.

Okazaki, H. N. Ishizaka, T. Sakurai, K. Kurokawa, K. Goto, M. Kumada and Y. Takuwa (1993) *Biochem. Biophys. Res. Comm.* 190, 1104–1109.

Yamaguchi, F., M. Tokuda, O. Hatase, S. Brenner (1996) *Biochem. Biophys. Res. Comm.* 227, 608–614.

* cited by examiner

LPA ANALOGS AS AGONISTS OF THE EDG2 LPA RECEPTOR

This application claims benefit of Provisional No. 60/141,078 filed Jun. 25, 1999.

FIELD OF INVENTION

Applicant has probed the Edg2 lysophosphatidic acid (LPA) receptor with a series of LPA analogs to determine receptor activation. The present invention is drawn to a series of LPA analogs which function as Edg2 receptor agonists, and methods of using such compounds to activate the Edg2 receptor of the surface of a cell. The compounds of the invention comprise a glycerol backbone with an ester-linked saturated or unsaturated alkyl group containing 15–17 carbons in addition to the carbonyl, substitutions of the hydroxyl group (—OH) at carbon two of the glycerol backbone, and optional replacement of the phosphate di-anion with either a hydroxyl group or a dimethylated phosphate. These LPA analogs may find uses in cancer and neurological disorders.

BACKGROUND

Lysophosphatidic acid (O-acyl-2-hydroxyl-sn-glycero-3-phosphate, LPA) is an intensely studied lipid phosphoric acid mediator of many well characterized and diverse biological responses. Although certain pathways in which LPA acts as a signal have been studied, specific LPA receptors are not well understood. One of the difficulties associated with studying a particular effect of LPA is that most cells are in some way responsive to LPA, thus assigning a specific effect with a specific receptor has been problematic. Three receptors for LPA have been described in the literature; PSP24, Edg2 (also referred to as vzg1, $lp_{A1}$ and Gpcr26) and Edg4. Edg2 and Edg4 are a part of a small gene family of related receptors that currently has five members. Edg1, Edg3 and Edg5/H218 have been reported to be receptors for sphingosine-1-phosphate. PSP24, an LPA receptor from *X. leavies* and mice shares only 10% identity with Edg2 and is not considered to be a part of the Edg family. The following references are specifically incorporated herein in their entirety. An, S., M. A. Dickens, T. Bleu, O. G. Hallmark and E. J. Goetzl (1997) *Biochem. Biophys. Res. Comm.* 231, 619–622

An, S., T. Bleu, O. G. Hallmark and E. J. Goetzl (1998) Characterization of a novel subtype of human G protein-coupled receptor for lysophosphatidic acid. *J. Biol. Chem.* 273, 7906–7910

Erickson, J. R., J. J. Wu, J. G. Goddard, G. Tigyi, K. Kawanishi, L. D. Tomei and M. C. Kiefer (1998) Edg-2/vzg-1 couples to the yeast pheromone response pathway selectively in response to lysophosphatidic acid *J. Biol. Chem.* 273, 1506–1510

Fischer, D. J., K. Liliom, Z. Guo, N. Nusser, T. Virag, K. Murakami-Murofushi, S. Kobayashi, J. R. Erickson, G. Sun, D. D. Miller and G. Tigyi. (1998) Naturally occurring analogs of lysophosphatidic acid elicit different cellular responses through selective activation of multiple receptor subtypes. *Mol. Pharmacol.* 54:979–988

Guo, Z., K. Liliom, D. J. Fischer, I. C. Bathurst, L. D. Tomei, M. C. Kiefer and G. Tigyi (1996) Molecular cloning of a high-affinity receptor for the growth factor-like lipid mediator lysophosphatidic acid from Xenopus oocytes *Proc. Natl. Acad. Sci. USA* 93, 14367–14372

Hecht, J. H., J. A. Weiner, S. R. Post and J. Chun (1996) Ventricular zone gene-1 (vzg-1) encodes a lysophosphatidic acid receptor expressed in neurogenic regions of the developing cerebral cortex *J. Cell Biol.* 135, 1071–1083

Hopper, D. W., S. P. Ragan, S. B. Hooks, K. R. Lynch and T. L. Macdonald (1999) Structure-activity relationship of lysophosphatidic acid: Conformationally restricted backbone mimetics. *J. Med. Chem.* 42:963–970

Hooks, S. B., S. P. Ragan, D. W. Hopper, C. W. Honemann, M. E. Durieux, T. L. Macdonald and K. R. Lynch (1998) Characterization of a receptor subtype-selective lysophosphatidic acid mimetic. *Mol. Pharmacol.* 53, 188–194

Ishii, I., T. Izumi, H. Tsukamoto, H. Umeyama, M. Ui and T. Shimizu (1997) *J. Biol. Chem.* 272, 7846–7845

Jalink, K, T. Hengeveld, S. Mulder, F. R. Postma, M.-F. Simon, H. Chap, G. A. van der Marel, J. H. van Boom, W. J. van Blitterswijk and W. H. Moolenaar (1995) *Biochem. J.* 307, 609–616

Lee, M.-J., M. Evans and T. Hla (1996) *J. Biol. Chem.* 271, 11272–11279

Liliom, K., R. Bitttnan, B. Swords and G. Tigyi (1996) N-palmitoyl-serine and N-palmitoyl-tyrosine phosphoric acids are selective competitive antagonists of the lysophosphatidic acid receptors. *Mol. Pharmacol.* 50:616–623

Lynch, K. R., D. W. Hopper, S. J. Carlisle, J. G. Catalano, M. Zhang and T. L. Macdonald (1997) Structure/activity relationships in lysophosphatidic acid: The 2-hydroxyl moiety. *Mol. Pharmacol.* 52, 75–81

MacLennan, A. J., C. S. Browe, A. A. Gaskin, D. C. Lado and G. Shaw (1994) *Mol. Cell. Neurosci.* 5, 201–209

Macrae, A. D., R. T. Premont, M. Jaber, A. S. Peterson, R. J. Lefkowtiz (1996) *Mol. Brain Res.* 42, 245–254

Okazaki, H. N. Ishizaka, T. Sakurai, K. Kurokawa, K. Goto, M. Kumada and Y. Takuwa (1993) *Biochem. Biophys. Res. Comm.* 190, 1104–1109

Yamaguchi, F., M. Tokuda, O. Hatase, S. Brenner (1996) *Biochem. Biophys. Res. Comm.* 227, 608–614

All publications and patent applications mentioned in this specification are herein incorporated by reference to the same extent as if each individual publication or patent application was specifically and individually indicated to be incorporated by reference.

Although certain structure/activity relationships of LPA have been observed, the effects cannot be attributed to a particular or a single receptor because of the possibility that a particular analog could be signaling through different receptors to achieve the same phenotypic effect leading to conflicting results concerning the specific structure/activity relationship of LPA. Indeed, given that there are at least three LPA receptors present in mammalian cells and given the wide range of phenotypic responses to LPA, caution must be exercised when making such analysis.

A yeast expressing the Edg2 receptor is one way to avoid such problems of multiple receptors. Edg2 has been functionally expressed in the yeast *Saccharomyces cerevisiae* and provides a facile system with which to analyze this particular receptor. Edg2 couples to the yeast pheromone response pathway selectively in response to exogenously added LPA and activates two easily assayed reporter genes, lacZ and HIS3, that are fused to the pheromone-inducible FUS1 promoter. Using the FUS1::lacZ reporter, Edg2 in yeast has been shown to selectively respond to LPA and not other glycerophospholipids. Although the yeast assay is relatively insensitive to LPA compared with mammalian signaling events (the yeast assay has an E.C.$_{50}$ of 20 μM), yeast offers the advantage of specificity; the induction of FUS1::lacZ by LPA is absolutely dependent on the Edg2 receptor being expressed.

SUMMARY OF INVENTION

Using a series of 17 LPA analogs that alter the length and saturation of the fatty acid side chain, the linkage between the fatty acid, the glycerol backbone, and the 2-hydroxyl moiety and the phosphate moiety the Edg2 receptor is analyzed pursuant to this invention and the molecular determinants of LPA in Edg2 receptor activation in yeast is established. Therefore, as a preliminary study to the analysis of the Edg2 receptor in mammalian cells, we established the molecular determinants of LPA in Edg2 receptor activation in yeast.

Thus, a primary aspect of this invention are compounds which act as Edg2 agonists. These compounds of the present invention have the formula:

wherein, X is hydroxyl,

Z is hydrogen, bromine, chlorine, fluorine, iodine, or OR$_2$, wherein R$_2$ is an unsaturated alkyl containing 1–3 carbons; and wherein R$_1$ is a saturated or unsaturated alkyl chain containing 15–17 carbons.

In preferred compounds of the present invention, X is phosphate. Also, in preferred compounds of the present invention, R$_1$ is a saturated or unsaturated alkyl chain containing 17 carbons. In other preferred embodiments, Z is hydrogen, bromine, or oxymethyl. Particular preferred embodiments of this aspect of the present invention include 1-(3-propyl oleate) phosphate, 3-O-oleoyl-2-O-methyl-rac-glycero-1-phosphate, 1-O-oleoyl-2-O-methyl-rac-glycerol, 3-O-oleoyl-2-deoxy-2-bromo-rac-glycero-1-phosphate, and 1-O-oleoyl-2-deoxy-2-bromo-rac-glycerol.

Another aspect of the present invention is the use of any of the above compounds to activate an Edg2 receptor on the surface of a cell. In this aspect of the invention, the Edg2 receptor presenting cell is exposed to an Edg2 receptor activating amount of the compounds of the invention. The preferred compound embodiments of the invention are also preferred for use in the Edg2 receptor activating method of the invention.

DETAILED DESCRIPTION OF THE INVENTION

The Edg2 lysophosphatidic acid (LPA) receptor, was probed with a series of LPA analogs to determine receptor activation. The Edg2 receptor has a strong requirement for an acyl-(ester) linkage between the glycerol backbone and the fatty acid side chain for activation of the FUS1::lacZ reporter in a yeast assay. Fatty acid side chains having specified lengths are measured for activity of the FUS1::lacZ reported. Substitutions of the hydroxyl group (—OH) at carbon two of the glycerol backbone with a hydrogen atom (—H), a methoxy group (—O—CH$_3$) or a bromine atom (—Br) and replacement of the phosphate di-anion with either a hydroxyl group or a dimethylated phosphate and demonstrated to retain FUS1::lacZ activity. Using specific LPA analogs, the activity profile of ERK½ MAP kinases were compared with the Edg2 activation of FUS1::lacZ in the yeast assay. Edg2 does not mediate ERK activity and the sn-2 substituted LPA analogues fit the criteria for Edg-2 specific agonists. These LPA analogs may find uses in cancer and neurological disorders.

Synthetic Routes of the Lysophosphatidic Acid Analogs-

Figure 1:
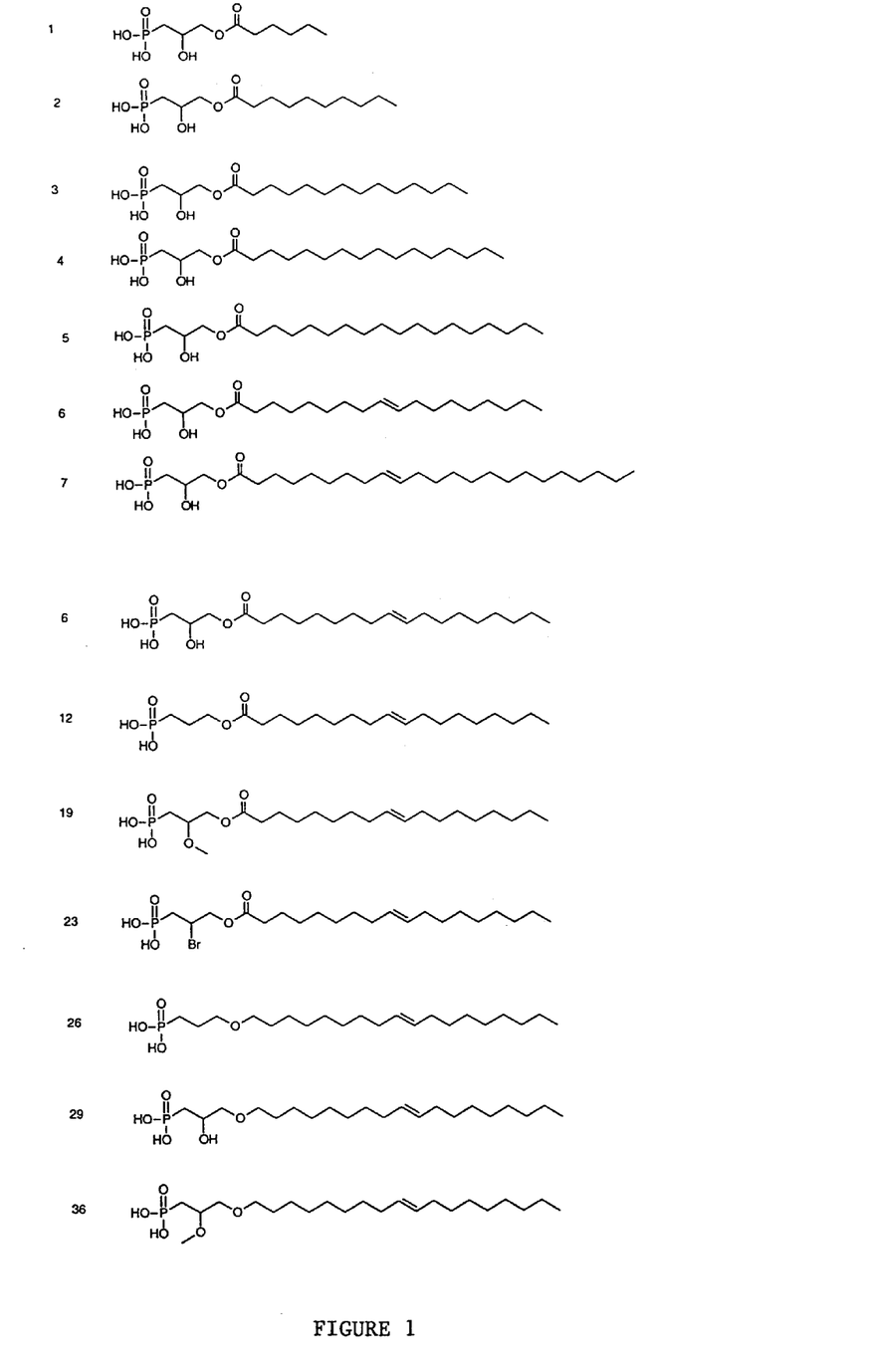
FIG. 1 is the structure of certain LPA analogs analyzed pursuant to the invention.
Figure 2:
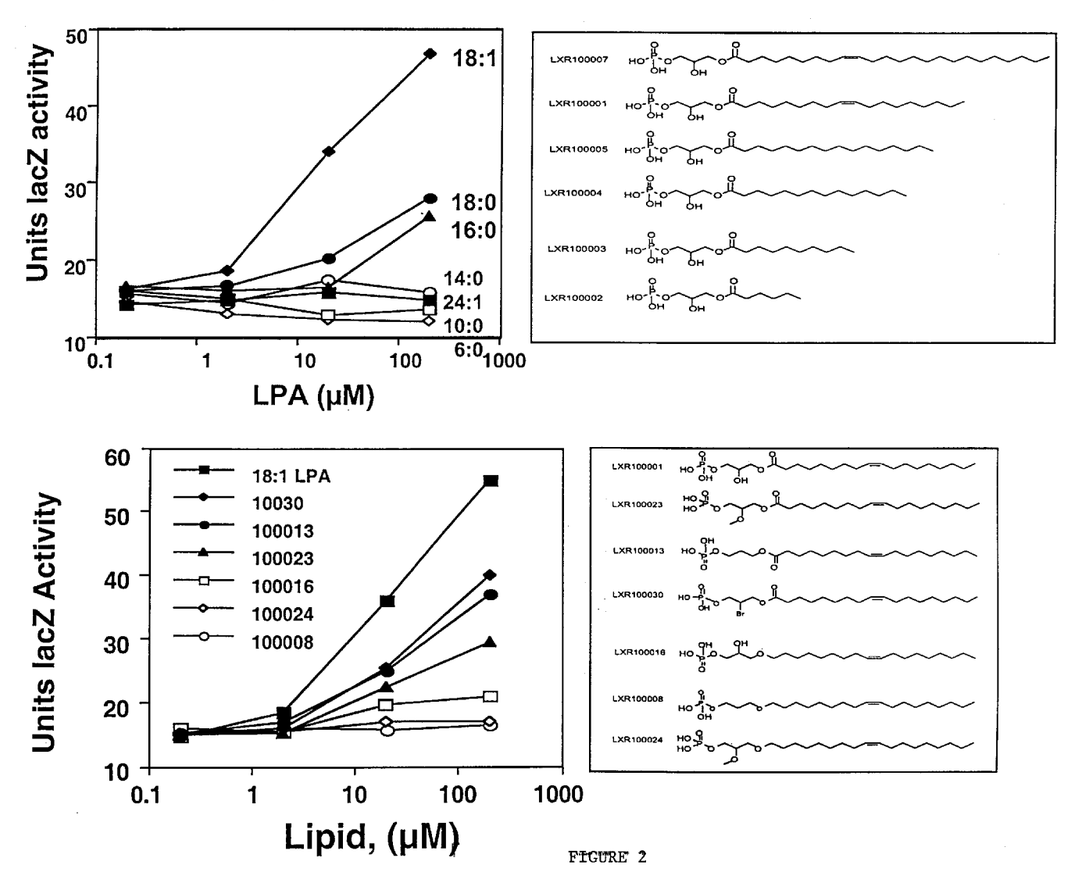
FIG. 2 shows the dependence of FUS1::lacZ activation an acyl chain length.
Figure 3:
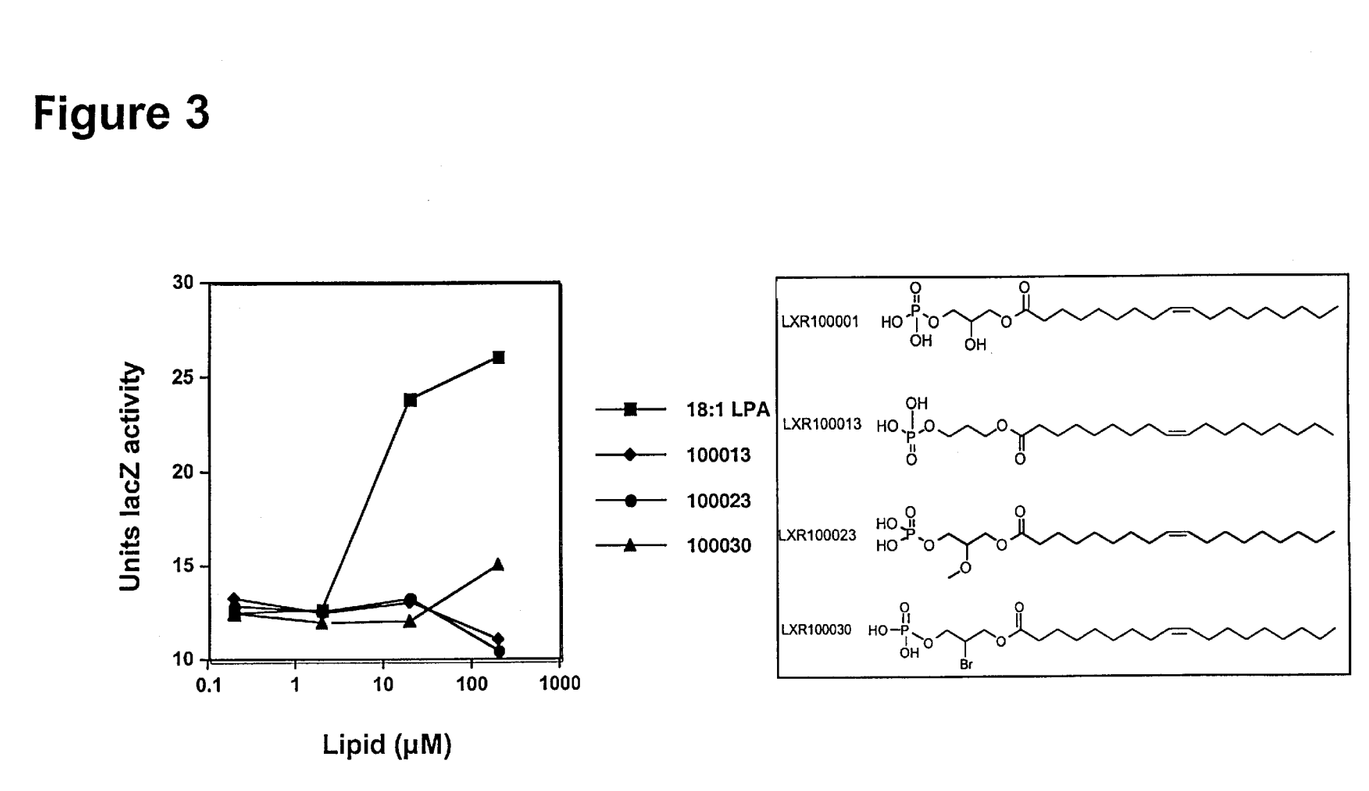
FIG. 3 shows the selected LPA analogs and the activation of FUS1::lacZ.

The structures of all of the LPA molecules and LPA analogs are shown in FIG. 1. The details of the synthetic routes, including spectral data, are reported in the Example. The compounds shown in FIG. 1 refer to all compounds tested and referred to in the text (see below). Activation of the Edg2 receptor is strongly dependent on the length of the fatty acid and the acyl-linkage- It is previously known that FUS1::lacZ could be activated in yeast expressing the Edg2 receptor by LPA molecules with 18 and 16 carbons with the mono-unsaturated 18:1 oleoyl form (6) being the most active although 18:0 (5) and 16:0 (4) did have significant activity. The shorter 6:0 (1) and 10:0 (2) carbon forms are known to be inactive. The data herein demonstrate that the 14:0 (3) and 24:1 (7) forms are also inactive in this system (see FIG. 2). This experiment places upper (18 carbons) and lower (16 carbons) limits to the length of the side chain that will activate FUS1::lacZ.

Figure 4:
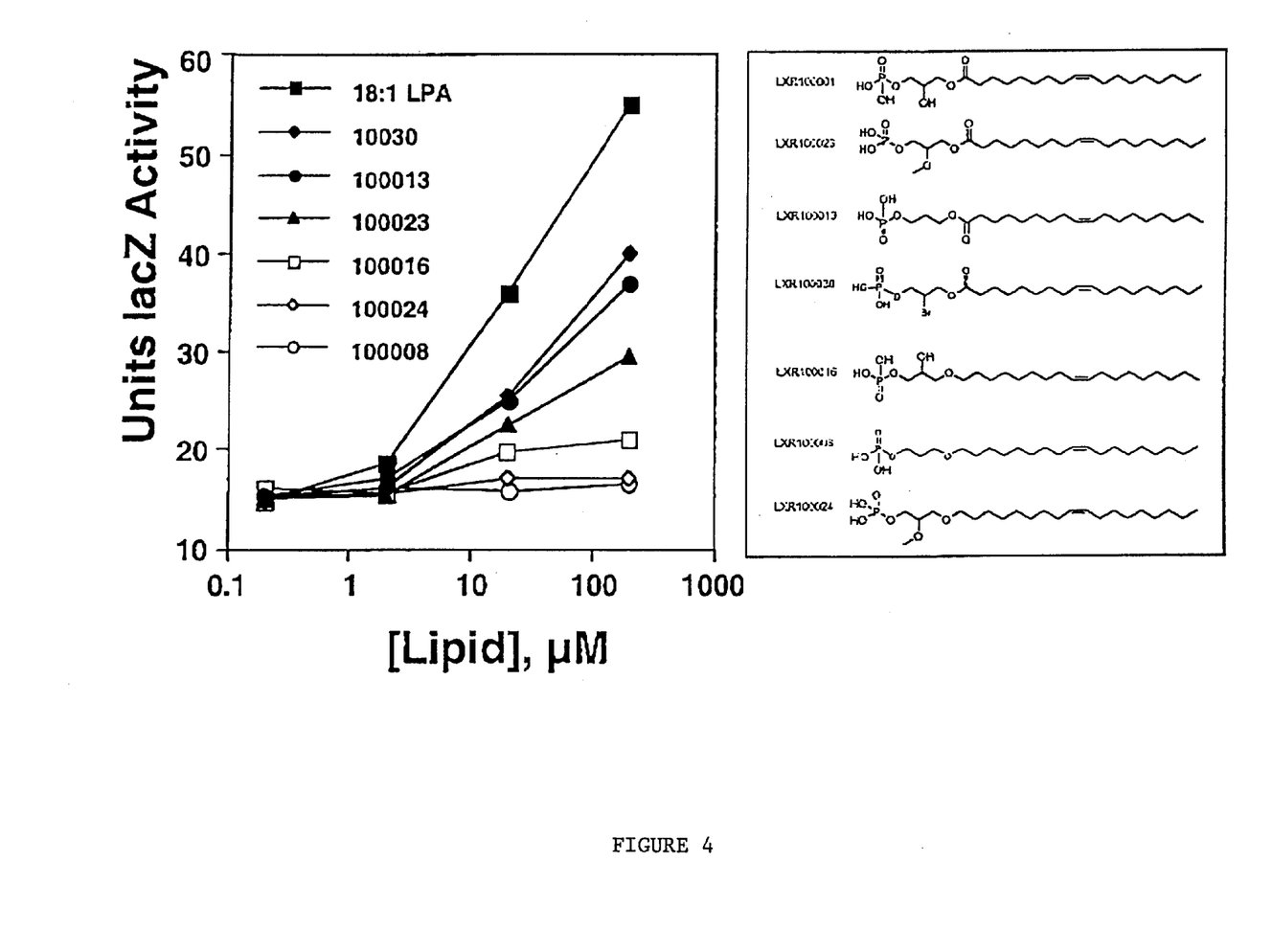
FIG. 4 is a comparison of all 18:1 analogs for FUS1::lacZ activation.

A series of LPA analogs were synthesized that would allow the comparison of the ester (acyl-) linkage to ether (alkenyl-) linked forms. Lysophosphatidic acid normally has a hydroxyl group on the sn-2 position of the glycerol moiety that can be esterified with another fatty acid to create phosphatidic acid. A series of substitutions at the sn-2 position were synthesized that replaced the hydroxyl group (—OH) with a proton (—H), a methoxy group (—O—CH3) or a Bromine atom (—Br). All of these analogs had an 18:1 oleoyl side chain linked to the sn-3 position of the racemic glycerol/propyl backbone. This yielded four ester-linked analogs (6, 12, 19 and 23) and three ether-linked analogs (26, 29, and 36) to compare in both the yeast lacZ reporter assay and MAP Kinase activation assay (see below). As seen in FIG. 4, activation of FUS1::lacZ in yeast is strongly dependent on the ester linkage. Ether linked forms were inactive in the yeast assay suggesting that the carbonyl oxygen to be important in receptor activation and/or ligand binding. The changes at the two position of the glycerol had less severe effects that changing the fatty acid linkage. All three acyl-linked analogs (12, 19 and 23) all retained some FUS1::lacZ activity in yeast suggesting the hydroxyl group normally present at this position does not make critical contacts with the receptor whereas the carbonyl group in the linkage does make essential contacts.

We next tested the requirement of the free phosphate di-anion group on the activation of FUS1::lacZ using some of the synthetic precursors to the 2-deoxy acyl analog (12) and to the—O-methyl acyl analog (19). FIG. 4 compares the activity of FUS1::lacZ using 200 µM LPA or LPA analog using 18:1 acyl LPA as 100%. The precursors that were used either lacked the phosphate altogether or had methyl-blocked phosphate groups. Interestingly, the analogs that lacked the phosphate completely (10, 17) still retained some lacZ activity. The addition of the methyl-blocked phosphate group (11, 18) had less lacZ activity in both cases. The subsequent removal of the blocking methyl-groups to complete the analog increased activity significantly (12, 19). Note that the 2-deoxy and —O-methyl acyl-linked precursors that either lacked a phosphate or have methyl-blocked phosphate groups retain more activity than their alkenyl-linked counterparts that have a free phosphate group (29 and 36). This reinforces that importance of the acyl linkage in Edg2 activation.

Figure 5:
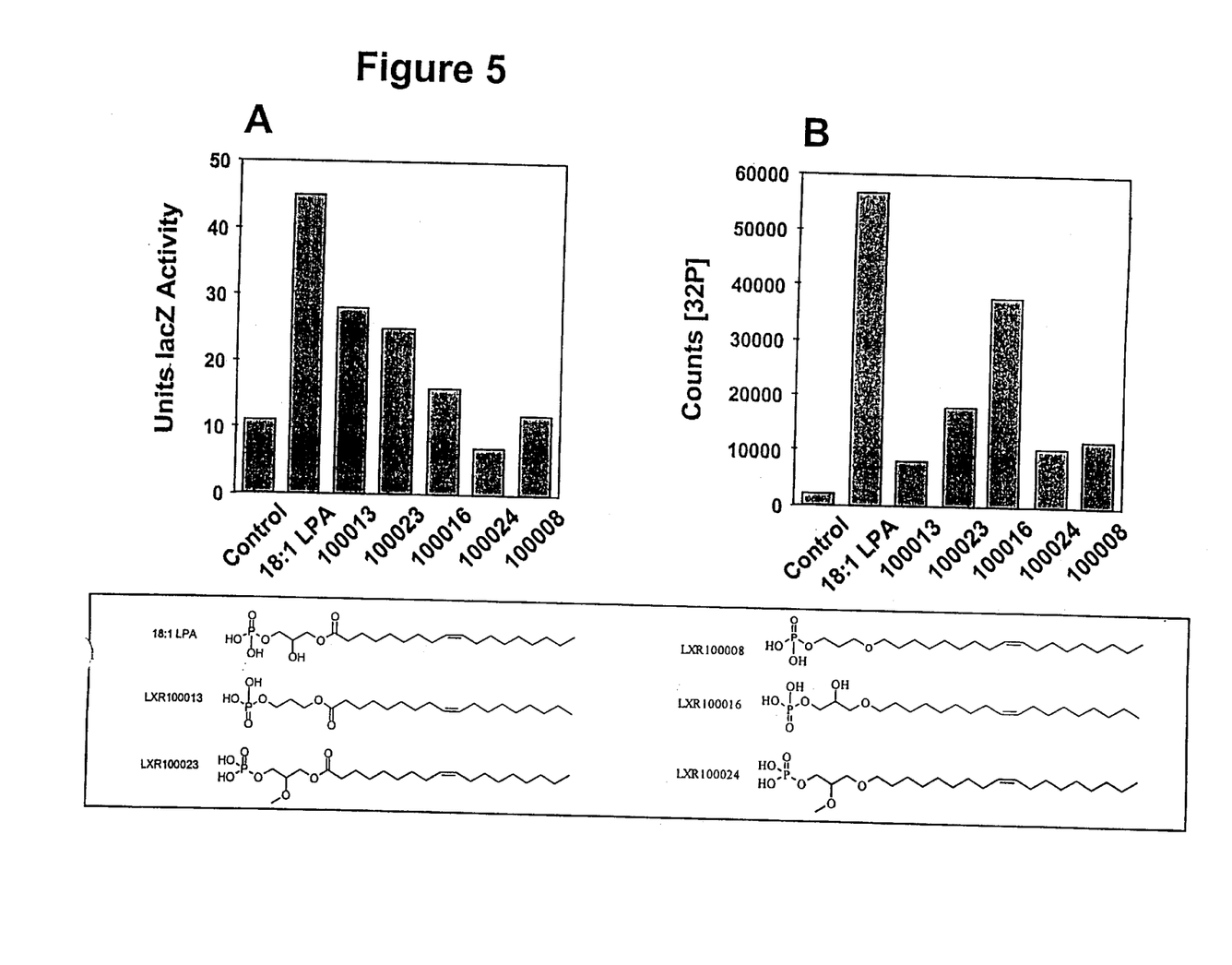
FIG. 5 shows the activation of ERK½ in C3H/10T½ fibroblasts by LPA analogs.

The SAR of LPA suggests that Edg2 does not activate MAP Kinase- The yeast GPA1 gene product is most similar to the $G_{\alpha i}$ class of alpha subunits. Since Edg2 couples to Gpa1, this receptor could also couple to $G_i$ in mammalian cells as well. A subset of LPA analogs were tested for the activation of ERK1 and ERK2 that are known to be activated by LPA in a Pertusis toxin-sensitive ($G_i$) manner and compared these results with FUS1::lacZ activation in yeast. Murine C3H/10T½ fibroblasts were treated with 10M analogue and assayed for induction of ERK½ activity. The results of one such experiment are shown in FIG. 5. It is apparent from these results that the structure/activity profile of ERK activation does not match the profile for the activation of FUS1::lacZ in the yeast system. The structural requirements of LPA with respect to ERK activation are quite different from the yeast Edg2 lacZ reporter assay. For example, the hydroxyl on the sn-2 carbon of the glycerol can be substituted with little effect in the Edg2-mediated activation of FUS1::lacZ whereas in ERK activation, loss of this hydroxyl almost completely abolishes activity. Furthermore, the 18:1 ether-linked (alkenyl) form can activate ERK almost as well as the ester form. This is in contrast to the Edg2 situation where alkenyl forms failed to activate the lacZ reporter. Taken together, these data strongly suggest that the Edg2 receptor does not activate ERK.

Four main conclusions can be drawn from the data herein. First, activation of Edg2 by LPA requires a fatty acid side chain of 16–18 carbons. LPA forms with longer (24) and shorter (14) carbon lengths were inactive. Second, the ester (acyl-) linkage is probably the most important structural determinant for receptor activation. Ether linked analogues tend to have little or no activity. There are two possible explanations for this effect. The carbonyl group could make important contacts with amino acids in the receptor that result in receptor activation or the ester linkage creates an optimal geometric relationship between the glycerol backbone and the fatty acid side chain. In this report we show that ether-linked analogs that have a mono-unsaturated bond between the 9th and 10th carbons of the 18-carbon chain do not activate Edg2.

However, it is also known a vinyl-ether-linked form (the mono-unsaturated bond is between the first and second carbons, immediately next to the ether linkage) does activate FUS1::lacZ. This vinyl ether form of LPA (more correctly termed alkenyl-glycerol phosphate) was originally purified from commercial sphingolipid preparations and has many LPA-like activities. The difference between the vinyl-ether and non-vinyl-ethers would suggest a structural conformation of the lipid molecule that would improve its binding to the activated state of the receptor. However, it is also likely that the carbonyl oxygen could also make a critical contact with the receptor.

Thirdly, the hydroxyl group on the number two carbon is not necessary for activation of Edg2. Substitutions of this moiety still permit activation of FUS1::lacZ although at less than is attainable with LPA. Finally, the role of the free phosphate is also not necessary for activation. Using synthetic intermediates, we noticed that analogs completely lacking a phosphate and only having a hydroxyl group at the third position can still activate FUS1::lacZ. Replacing the phosphate with the hydroxyl results in a loss of activity nearly equivalent to substituting the second position hydroxyl group. Blocking the phosphate with methyl groups further attenuates FUS1::lacZ activation. No analogs tested showed improved activation of FUS1::lacZ over 18:1 LPA so it is reasonable to conclude that maximal activation of Edg2 is the contribution of the ester linkage, the length of the side chain, the 2-hydroxyl moiety and the free phosphate di-anion with the ester linkage being the most important.

Lynch and co-workers reported on a different SAR study of LPA with respect to $Ca^{2+}$ mobilization and cAMP accumulation in MDA MB 231 cells. This study examined the role of the sn-2 hydroxyl and the overall length of the molecule. In their report, they show that an overall length of 24–25 molecules is optimal, consistent with our observations that fatty acid chain length of 16–18 (or an overall length of 23–25 molecules) is optimal in the yeast Edg2 assay. Although only one common analog exist, the 2-deoxy ester analog (12), this compound does activate FUS1::lacZ in the yeast, it does not inhibit cAMP accumulation and only slightly mobilizes calcium in the MDA MB 231 cells. This is consistent with the data showing that compound 12 does not activate ERK (see FIG. 5) in the C3H10T½ fibroblasts and therefor probably does not activate a $G_i$-coupled receptor in these cells. It has been recently reported that Edg2 will directly interact with $G_i$ as well as other G proteins suggesting a possible promiscuous role for this receptor. However, no specific functional role for Edg2 has been identified that would unequivocally assign it to a particular class of G-protein signaling. Although Edg2 does not appear to signal to ERK and adenyl cyclase, which are known to be $G_i$-mediated, it does couple to the yeast Gpa1 which is most closely related to the $G_i$ class of alpha subunits.

Edg2 is not involved in the activation of the MAPKinase ERK. This is somewhat surprising since Edg2 coupled to the endogenous Saccharomyces G-protein, it was reasonable to conclude that Edg2 may couple to mammalian $G_i$ heterotrimeric G-proteins. If this were true, then Edg2 would activate ERK, which is activated by LPA in a pertusis toxin-dependent manner. However, the SAR of LPA for ERK activation is completely different from the SAR of LPA-mediated activation of FUS1::lacZ and calcium mobilization. It is unlikely that expressing this receptor in yeast has changed its ligand binding characteristics. The somatostatin 2A receptor when expressed in yeast maintains it's binding profiles when compared with mammalian cells. Therefore, since the activation profiles of Edg2 in yeast and ERK in fibroblasts are different, Edg2 does not activate ERK. This is supported by the observation that in the A549 lung carcinoma, which overexpresses the Edg2 mRNA, LPA does not stimulate ERK activity.

The following example is provided to illustrate the various aspects of the invention, and should not be interpreted to limit the invention to particular embodiments. Variations and modifications of the present invention will be apparent to those of ordinary skill in the art, and so such modifications are considered to be encompassed by the scope of the present invention.

EXAMPLE

SYNTHESIS AND CHARACTERIZATION OF LPA ANALOGS

The 6:0, 10:0, 14:0, 16:0, 18:0, 18:1, and 24:1 acyl-LPA analogs were obtained from Avanti Polar Lipids (Alabaster, Ala.).

Synthesis of 1-(3-propyl oleate) phosphate (12)
3-Hydroxypropyl oleate (10)

To a solution of 1,3-propanediol (3.61 mL, 50.0 mmol) in pyridine (100 mL) was added chlorotriphenylmethane (14 g, 50.0 mmol) and the mixture was stirred at 70° C. for 16 h. The solvent was removed by co-evaporation with dry toluene (2×50 mL) and the resulting residue was redissolved in diethyl ether (150 mL), washed with $H_2O$ (2×50 mL), dried ($MgSO_4$), concentrated and purified by silica-gel column chromatography [eluent: hexane/ethyl acetate, 90/10, v/v] to give monotritylated diol 8. $^1H$ NMR (360 MHz; $CDCl_3$): δ 1.82 (2 H, quintet, J 6 Hz, 2-$H_2$), 3.23 (2 H, t, J 6 Hz, 1-$H_2$ or 3-$H_2$), 3.72 (2 H, t, J 5.5 Hz, 1-$H_2$ or 3-$H_2$), 7.18–7.28 (10 H, m, 2×Ph) and 7.34–7.40 (5 H, m, Ph).

To a solution of compound 8 (3.2 g, 10 mmol) and DMAP (50 mg) in pyridine (10 mL) was added oleoyl chloride (3.3 g, 10 mmol). After 4 h, pyridine was removed by co-evaporation with dry toluene (2×50 ml) and the obtained residue was partitioned between diethyl ether (150 mL) and $H_2O$ (50 mL), The diethyl ether layer was subsequently washed with sat. NaCl (50 mL) dried ($MgSO_4$) and evaporated to dryness. The residue was purified by silica-gel column chromatography [eluent: hexane/diethyl ether, 90/10, v/v] to give trityl ester 9.

Treatment of a solution of derivative 9 (3.72 g, 6.39 mmol) in dry $CH_2Cl_2$ (100 mL) with trifluoroacetic acid (5 mL) resulted in a bright yellow solution. Subsequently, the addition of H2O (10 mL) and solid NaHCO3 (5 g) quenched the mixture. The product was extracted into $CH_2Cl_2$ (2×100 mL), the organic phases were combined, dried ($MgSO_4$) and concentrated. Purification of the residue by silica-gel column chromatography [eluent: ethyl acetate/hexanes, 30/70, v/v] furnished the title alcohol (10) (2.1 g, 95%) as an oil. $^1H$ NMR (360 MHz; $CDCl_3$): δ 0.87 (3 H, t, J7 Hz, Me), 1.28 (20 H, apparent br d, separation 13.5 Hz, —$(CH_2)_4$— and —$(CH_2)_6$—), 1.60–1.63 (2 H, m, —$H_2$), 1.86 (2 H, quintet, J 6 Hz, 2-$H_2$), 1.98–2.01 (4 H, m, —$CH_2CH=CHCH_2$—), 2.31 (2 H, t, J 7.5 Hz, —$H_2$), 3.68 (2 H, t, J 6 Hz, 3-$H_2$), 424 (2H, t, J 6 Hz, 1-$H_2$), and 5.29–5.39 (2 H, m, —$CH_2CH=CHCH_2$—).

Dimethyl 1-(3-propyl oleate) phosphate (11)

To a solution of alcohol 10 (0.52 g, 1.5 mmol) and N-methylimidazole (0.27 mL, 3.3 mmol) in dry $CH_2Cl_2$ (5 mL) was added dimethyl chlorophosphate (0.2 mL, 1.8 mmol). After 1 h, TLC analysis showed the reaction to be complete, sat. $KHSO_4$ (20 mL) was added and the mixture was extracted with ethyl acetate (3×50 mL), the combined organic phases were washed with sat. NaCl (40 mL) dried ($MgSO_4$) and concentrated. The residue was subjected to silica-gel column chromatography [eluent: ethyl acetate/ hexanes, 50/50, v/v] to give protected phosphate 11 as an oil. $^1H$ NMR (360 MHz; $CDCl_3$): δ 0.87 (3 H, t, J 7 Hz, Me), 1.28 (20 H, apparent br d, separation 13 Hz, —$(CH_2)_5$— and —$(CH_2)_6$—), 1.59–1.64 (2 H, m, —$H_2$), 1.98–2.04 (6 H, m, 2-$H_2$ and—$CH_2CH=CHCH_2$—), 2.30 (2 H, t, J 7.5 Hz, α$H_2$), 3.75 and 3.78 (each 3 H, s, 2×OMe), 4.11–4.20 (4 H, m, 1-$H_2$ and 3-$H_2$), 5.29–5.39 (2 H, m, —$CH_2CH=CHCH_2$—); $^{31}P$ NMR (146 MHz; $CDCl_3$): δ 2.54; ESI-MS (m/z, +ve): 449 ($MH^+$, 100%) and 466 ($M+18^+$, 89).

1-(3-propyl oleate) phosphate (12)

To a stirring solution of dimethyl phosphate 11 (0.31 g, 0.7 mmol) in dry $CH_2Cl_2$ (4 mL) was added BSA (0.52 mL, 2.1 mmol) followed by the addition of TMSBr (0.19 mL, 1.4 mmol). After 30 min, TLC analysis showed complete consumption of the starting material, the reaction was quenched with 1/1 $MeOH/H_2O$ (1 mL, 1/1) for 30 min, followed by the addition of sat. $KHSO_4$ (5 mL). The mixture was extracted with ethyl acetate (2×30 mL), the organic extracts were combined, dried ($MgSO_4$) and evaporated to dryness. Purification of the residue by Sephadex LH-20 column chromatography [eluent: $MeOH/CH_2Cl_2$, 50/50, v/v] gave the title phosphate (12) as an oil. $^1H$ NMR (360 MHz; $CDCl_3$): δ 0.87 (3 H, t, J 7 Hz, Me), 1.28 (20 H, apparent br d, separation 11 Hz, —$(CH_2)_4$— and —$(CH_2)_6$—), 1.57–1.61 (2 H, m, —$H_2$), 2.00 (6 H, apparent br d, separation 3.5 Hz, —$CH_2CH=CHCH_2$— and 2-$H_2$), 2.30 (2 H, t, J 7.5 Hz, α-$H_2$), 4.11 (2 H, quartet, J 6 Hz, 3-$H_2$), 4.19 (2 H, t, J 6.5 Hz, 1-$H_2$), 5.29–5.38 (2 H, m, —$CH_2CH=CHCH_2$—) and 9.24 (2 H, br s, 2×OH); $^{31}P$ NMR (146 MHz; $CDCl_3$): 1.80; ESI-MS (m/z, -ve): 419 ($M-H^+$, 100%)

Synthesis of 3-O-Oleoyl-2-O-methyl-rac-glycero-1-phosphate (19)

1-O-Oleoyl-2-O-methyl-rac-glycerol (17)

To a mixture of 1-O-benzyl-glycerol (27 mL, 0.16 mol) and t-butyldimethylsilyl chloride (25 g, 0.17 mol) in dry, $CH_2Cl_2$ (250 mL) under $N_2$ was added DMAP (0.8 g, 6.6 mmol) followed by the addition of TEA (23 mL, 0.17 mol). After 3 h, the mixture was washed with $H_2O$ (2×100 mL), dried ($MgSO_4$) and concentrated to give 1-Obenzyl-3-O-t-butyldimethylsilyl-rac-glycerol (13) (48.8 g, 100%) as a yellow oil.

$^1H$ NMR (360 MHz; $CDCl_3$): δ 0.06 (6 H, s, $Me_2Si$), 0.89 (9 H, s, $Bu^tSi$), 3.48–3.56 (2 H, m, 1-$H_2$ or 3-$H_2$), 3.64 (1 H, dd, J 10 and 5.5 Hz, 1-H or 3-H), 3.68 (1 H, dd, J 10 and 5 Hz, 1-H or 3-H), 3.86 (1 H, quintet, J 5.5 Hz, 2-H), 4.56 (2 H, s, —$OCH_2Ph$) and 7.27–7.35 (5 H, m, —Ph).

Alcohol 13 (48.8 g, 0.16 mmol) was added to a mixture of NaH (4.0 g, 0.17 mol) in dry THF (500 mL). After 5 min, MeI (10 mL, 0.17 mol) was added and, after another 3 h, the mixture was quenched with $H_2O$ (150 mL), extracted into diethyl ether (500 mL), dried ($MgSO_4$) and concentrated. Purification of the residue by silica-gel column chromatography [eluent: hexane/ethyl acetate, 90/10, v/v] yielded 1-O-benzyl-3-O-t-butyldimethylsilyl-2-O-methyl-rac-glycerol (14) (37 g, 74%) as a yellow oil.

$^1H$ NMR (360 MHz; $CDCl_3$): δ 0.05 and 0.05 (each 3 H, s, $Me_2Si$), 0.88 (9 H, s, $Bu^tSi$), 3.42 (1H, apparent quintet, separation 4.5 Hz, 2-H), 3.47 (3 H, s, OMe), 3.51 (1 H, dd, J 10 and 5.5 Hz, 1-H or 3-H),), 3.61(1 H, dd, J 10 and 4Hz, 1-H or 3-H), 3.68 (2 H, d, J 5.5 Hz, 1-H or 3-H), 4.54 (2 H, apparent d, separation 12 Hz, —OCHHAr), 4.58 (2 H, apparent d, separation 12 Hz, —OCHHAr), 7.28 (1 H, m,p-H) and 7.34 (4 H, apparent d, separation 4.5 Hz, o-$H_2$ and m-$H_2$); ESI-MS (m/z, +ve): 333 ($MNa^+$, 160%).

A mixture of the protected glycerol derivative 14 (5.0 g, 16 mmol) and 10% palladium on activated carbon (wet Degussa type E101 NE/W) (0.43 g) in MeOH (50 mL) was evacuated using an aspirator pump and filled with hydrogen. After 2 h, TLC analysis showed the reaction to be complete, the mixture was filtered through Celite and the filtrate was evaporated to dryness to give 1-O-t-butyldimethylsilyl-2-O-methyl-rac-glycerol (15) (99%) as a colourless oil.

$^1$H NMR (360 MHz; CDCl$_3$): δ 0.07 (6 H, s, Me$_2$Si), 0.89 (9 H, s, BU$^t$Si), 3.30–3.36 (1 H, m, 2-H), 3.46 (3 H, s, OMe), 3.63 (1 H, dd, J 11.5 and 5.5 Hz, 1- or 3-H), 3.65 (1 H, dd, J 10.5 and 6.5 Hz, 1- or 3-H), 3.74 (1 H, dd, J 105 and 5 Hz, 1- or 3-H) and 3.75 (1 H, dd, J 11.5 and 4 Hz, 1- or 3-H).

To a solution of alcohol 15 (1.1 g, 5.0 mmol) in CH$_2$Cl$_2$ (10 mL) was added oleoyl chloride (1.8 mL, 5.5 mmol) followed, after 5 min, by the addition of pyridine (0.44 mL, 5.5 mmol). After TLC analysis indicated that the reaction had gone to completion, the mixture was partitioned between ethyl acetate (100 mL) and H$_2$O (30 mL), the organic extract was dried (MgSO$_4$) and concentrated to give 1-O-t-butyldimethylsilyl-2-O-methyl-3-O-oleoyl-rac-glycerol (16) (2.4 g, 99%) as a dark brown oil.

$^1$H NMR (360 MHz; CDCl$_3$): δ 0.06 (6 H, s, Me$_2$Si), 0.88 (3 H, t, J 7 Hz, Me), 0.89 (9 H, s, Bu$^t$Si), 1.28 (20 H, apparent br d, separation 11.5 Hz, —(CH$_2$)$_4$— and —(CH$_2$)$_6$—), 1.60–1.64 (2 H, m, α-H$_2$), 1.98–2.03 (4 H, m, —CH$_2$CH=CHCH$_2$—), 2.33 (2 H, t, J 7.5 Hz, —H$_2$), 3.41–3.46 (1 H, br t, 2-H), 3.45 (3 H, s, OMe), 3.64 (1 H, dd, J 10.5 and 6 Hz, 3-H), 3.68 (1 H, dd, J 10.5 and 5.5 Hz, 3-H), 4.09 (1 H, dd, J 11.5 and 5.5 Hz, 1-H), 4.27 (1 H, dd, J 11.5 and 4 Hz, 1-H) and 5.32–5.36 (2 H, m, —CH$_2$CH=CHCH$_2$—).

1M TBAF (6 mL, 6.0 mmol) was added to a solution of compound 16 (2.4 g, 5.0 mmol) in THF (50 mL). After 30 min, TLC analysis showed that all the starting material had been consumed. Then, the reaction mixture was partitioned between diethy ether (100 mL and sat. NaCl solution (30 mL). The organic extract was dried (MgSO$_4$), concentrated and subjected to silica-gel column chromatography (eluent: hexane/ethyl acetate, 75/25, v/v] to give glycerol derivative 17 (1.42 g, 79%) as an oil $^1$H NMR (360 MHz; CDCl$_3$): δ 0.88 (3 H, t, J 7 Hz, Me), 1.29 (20 H, apparent br d, separation 13 Hz, —(CH$_2$)$_4$— and —(CH2)$_6$—), 1.60–1.64 (2 H, m, α-H$_2$), 1.98–2.03 (4 H, m, —CH$_2$CH=CHCH$_2$—), 2.33 (2 H, t, J 7.5 Hz, —H$_2$), 3.45–3.51 (1 H, br t, 2-H), 3.47 (3 H, s, OMe), 3.61 (1 H, dd, J 11.5 and 6 Hz, 3-H), 3.69 (1 H, dd, J 11.5 and 4.5 Hz, 3-H), 4.20 (2 H, apparent d, separation 5 Hz, 1-H$_2$) and 5.29–5.39 (2 H, m, —CH$_2$CH=CHCH$_2$—).

Dimethyl 3-O-oleoyl-2-O-methyl-rac-glycero-1-phosphate (18)

To a solution of alcohol 17 (0.79 g, 2.2 mmol) in dry CH$_2$Cl$_2$ (8 mL) was added N-methylimidazole (0.2 mL, 2.4 mmol) followed by the addition of dimethyl chlorophosphate (0.26 mL, 2.4 mmol). After stirring for 1 h, the mixture was quenched with sat. KHSO$_4$ (20 mL) and extracted into ethyl acetate (3×50 mL). The combined organic phases were subsequently washed with sat. NaCl (40 mL), dried (MgSO$_4$), concentrated and subjected to silica-gel column chromatography [eluent: ethyl acetate/hexanes, 50/50, v/v] to give protected phosphate 18 as an oil.

$^1$H NMR (360 MHz; CDCl$_3$): δ 0.87 (3 H, t, J 7 Hz, Me), 1.28 (20 H, apparent br d, separation 12.5 Hz, —(CH$_2$)$_4$— and —(CH$_2$)$_6$—), 1.60–1.64 (2 H, m, —β-H$_2$), 1.98–2.01 (4 H, m, —CH$_2$CH=CHCH$_2$—), 2.33 (2 H, t, J 7.5 Hz, α-H$_2$), 3.47 (3 H, s, OMe), 3.61 (1 H, quintet, J 5 Hz, 2-H), 3.76 (3 H, d, J 2 Hz, OMe), 3.80 (3 H, d, J 2 Hz, OMe), 4.05–4.19 (3 H, m, 1-H$_2$ or 3-H$_2$ and 3-H or 1-H), 4.25 (1 H, dd, J 12 and 4.5 Hz, 1-H or 3-H) and 5.29–5.39 (2 H, m, —CH$_2$CH=CHCH$_2$—); $^{31}$P NMR (146 MHz; CDCl$_3$): 2.52; ESI-MS (m/z, +ve): 479 (MH$^+$, 100%) and 496 (M+18$^+$, 83).

3-O-Oleoyl-2-O-methyl-rac-glycero-1-phosphate (19)

To a solution of dimethyl phosphate 18 (0.10 g, 0.22 mmol) in dry CH$_2$Cl$_2$ (5 mL) was added BSA (0.16 ml, 0.65 mmol) followed by the addition of TMSBr (60 μL, 1.4 mmol). After 30 min, the reaction was treated with 1/1 MeOH/H$_2$O (1 mL, v/v) for 30 min after which sat. KHSO$_4$ (5 mL) was added. The mixture was subsequently extracted with ethyl acetate (2×30 mL), the combined organic extracts were dried (MgSO$_4$), concentrated and subjected to Sephadex LH-20 column chromatography [eluent: MeOH/CH$_2$Cl$_2$, 50/50, v/v] to give the title phosphate (19) as an oil.

$^1$H NMR (360 MHz; CDCl$_3$): δ 0.86–0.87 (3 H, m, Me), 1.28 (20 H, apparent br d, separation 12 Hz, —(CH$_2$)$_4$— and —(CH$_2$)$_6$—), 1.61 (2 H, br s, β-H$_2$), 2.00 (4 H, apparent br d, separation 5 Hz, —CH$_2$CH=CHCH$_2$—), 2.34 (2 H, t, J 7.5 Hz, α-H$_2$), 3.48 (3 H, s, OMe), 3.66 (1 H, br s, 2-H), 4.15 (3 H, m, 1-H$_2$ or 3-H$_2$ and 3-H or 1-H), 4.27 (1 H, m, 1-H or 3-H), 5.30–5.34 (2 H, m, —CH$_2$CH=CHCH$_2$—) and 8.41 (1 H, br s, 2×OH); $^{31}$P NMR (146 MHz; CDCl$_3$) 1.82; ESI-MS (m/z, –ve): 449 (M-H$^+$, 100%) and 463 (MNa$^+$, 37).

Synthesis of 3-O-Oleoyl-2-deoxy-2-bromo-rac-glycero-1-phosphate (23)

Dimethyl3-O-oleoyl-2-deoxy-2-bromo-rac-glycero-1-phosphate (22)

To a stirring solution of 1-O-benzyl-2-deoxy-2-bromo-rac-glycerol (0.5 g, 2.0 mmol), dimethyl chlorophosphate (270 μL, 2.5 mmol) in dry CH$_2$Cl$_2$ (20 mL) under N$_2$ was added N-methylimidazole (180 μL, 2.2 mmol). After 3 days, the mixture was concentrated and purified by silica-gel column chromatography [eluent: ethyl acetate/hexane, 50/50, v/v] to yield dimethyl 3-O-benzyl-2-deoxy-2-bromo-rac-glycero-1-phosphate (20) (0.43 g, 59%) as an oil.

$^1$H NMR (360 MHz; CDCl$_3$): δ 3.73–3.81 (2 H, m, 3-H$_2$), 3.75 (3 H, apparent d, separation 13.5 Hz, OMe), 3.78 (3 H, apparent d, separation 14 Hz, OMe), 4.21 (1 H, quintet, J 5.5 Hz, 2-H), 4.28–4.40 (2 H, m, 1-H$_2$), 4.57 (2 H, br s, —OCH$_2$Ph) and 7.26–7.37 (5 H, m, —Ph); $^{31}$P NMR (146 MHz; CDCl$_3$): 1.88; ESI-MS (m/z, +ve): 353 and 355 (MH$^+$, 100%).

A mixture of bromo compound 20 (0.43 g, 1.2 mmol) and 10% palladium on activated carbon (0.43 g) in ethyl acetate (50 mL) was evacuated using an aspirator pump and filled with hydrogen. After 2 h, TLC analysis showed the reaction to be complete and the mixture was filtered through Celite. The filtrate was evaporated to dryness to furnish dimethyl 2-deoxy-2-bromo-rac-glycero-1-phosphate (21) (0.28 g, 88%) as colourless oil.

$^1$H NMR (360 MHz; CDCl$_3$): δ 2.35 (1 H, br s, OH), 3.80 (3 H, d, J 7 Hz, OMe), 3.83 (3 H, d, J 6.5 Hz, OMe), 3.89 (1 H, dd, J 12.5 and 6 Hz, 3-H), 3.94 (1 H, dd, J 12.5 and 5 Hz, 3-H), 4.13–4.19 (1 H, m, 2-H), 4.31 (1 H, ddd, J 11.5, 9.5 and 6 Hz, 1-H) and 4.46 (1 H, ddd, J 11.5, 9 and 4.5Hz, 1-H).

To a solution of alcohol 21 (0.28 g, 1.1 mmol) in dry CH$_2$Cl$_2$ (5 mL) under N$_2$ was added oleoyl chloride (0.39 mL, 1.2 mmol) followed by the addition of pyridine (0.09 mL, 1.2 mmol). After 1 h, the mixture was concentrated and subjected to silica-gel column chromatography [eluent: ethyl acetate (20–50%) in hexane, v/v] to give phosphate 22 (0.48 g, 85%) as an oil.

$^1$H NMR (360 MHz; CDCl$_3$): δ 0.86 (3 H, t, J7 Hz, Me), 1.25 (20 H, apparent doublet, separation 14 Hz, —(CH$_2$)$_4$— and —(CH$_2$)$_6$—), 1.58–1.62 (2 H, m, —H$_2$), 1.97–1.98 (4 H, m, —CH$_2$CH=CHCH$_2$—), 2.33 (2 H, t, J 7.5 Hz, α-H$_2$), 3.76 (3 H, d, J 1.5 Hz, OMe), 3.79 (3 H, d, J 2 Hz, OMe), 4.20–4.31 (3 H, m, 2-H and 3-H$_2$), 4.36 (1 H, dd, J 12 and 5 Hz, 1-H), 4.40 (1 H, dd, J 12 and 5.5 Hz, 1-H) and 5.26–5.36 (2 H, m, —CH$_2$CH=CHCH$_2$—); $^{31}$P NMR (146 MHz; CDCl$_3$): 1.82; ESI-MS (m/z, +ve): 527 and 529 (MH$^+$, 29%), 549 and 551 (MH$^+$, 49) and 565 and 567 (MH$^+$, 100).

3-O-Oleoyl-2-deoxy-2-bromo-rac-glycero-1-phosphate (23)

To a solution of bromo alcohol 22 (0.20 g, 0.38 mmol) in dry CH$_2$Cl$_2$ (20 mL) under N$_2$ was added BSA (0.21 ml, 0.83 mmol) followed by the addition of TMSBr (0.11 mL, 0.83 mmol). The reaction was carefully monitored by TLC and after 85 min all the starting material had been consumed. Then, 1/1 MeOH/H$_2$O (3 mL, v/v) was added and the mixture was stirred for a subsequent 15 min after which sat. KHSO$_4$ (5 mL) was added. The mixture was subsequently extracted with ethyl acetate (3×10 mL), the organic extracts were combined, dried (MgSO$_4$), concentrated and subjected to Sephadex LH-20 column chromatography [eluent: MeOH/CH$_2$Cl$_2$, 50/50, v/v] to give the title phosphate (23) (0.19 g, 99%) as a yellow oil.

$^1$H NMR (360 MHz; CDCl$_3$): δ 0.87 (3 H, t, J 7 Hz, Me), 1.28 (20 H, apparent doublet, separation 13.5 Hz, —(CH$_2$)$_4$— and —(CH$_2$)$_6$—), 1.61–1.62 (2 H, m, —H$_2$), 1.99–2.01 (4 H, m, —CH$_2$CH=CHCH$_2$—), 2.36 (2 H, t, J 7 Hz, α-H$_2$), 4.19–4.28 (3 H, m, 2-H and 3-H$_2$), 4.37 (1 H, dd, J 12 and 5 Hz, 1-H), 4.47 (1 H, dd, J 12 and 5 Hz, 1-H), 5.29–5.38 (2 H, m, —CH$_2$CH=CHCH$_2$—) and 9.05 (2 H, s, 2×OH); $^{31}$P NMR (146 MHz; CDCl$_3$): δ 1.08; ESI-MS (m/z, −ve): 499 and 501 (M-H$^+$, 100%).

Synthesis of 3-O-Oleyl-rac-glycero-1-phosphate (26)
1-O-Oleyl-glycidol (25)

To a solution of glycidyl tosylate (2.0 g, 8.8 mmol) and oleyl alcohol (1.88 mL, 7.0 mmol) in dry CH$_2$Cl$_2$ (40 mL) under N$_2$ was added a BF$_3$.OEt$_2$ solution (~2.2 mL, ~10% in CH$_2$Cl$_2$). After 48 h, TLC analysis showed the reaction to be complete and the solvent was removed in vacuo to give 1-O-oleyl-rac-glycero-3-p-toluenesulfonate (24) as an oil.

Crude 24 was taken up in 50% aq. MeOH (30 mL) to which NaOH (1.4 g, 35.0 mmol) was added. After 16 h, TLC analysis showed the reaction to be complete and the mixture was concentrated to remove MeOH. The remaining aqueous phase was extracted with diethyl ether (2×40 mL) and the combined organic phases were washed with H$_2$O (30 mL), sat. NaHCO$_3$ (30 mL), dried (MgSO$_4$) and concentrated. The residual oil was purified by silica-gel column chromatography [eluent: ethyl acetate/hexane, 91/9, v/v] to furnish epoxide 25 (1.65 g, 72%) as a colourless oil.

$^1$H NMR (360 MHz; CDCl$_3$): δ 0.88 (3 H, t, J 6.5 Hz, Me), 1.28 (22 H, apparent br d, separation 9 Hz, —(CH$_2$)$_5$— and —(CH$_2$)$_6$—), 1.58 (2 H, br s, β-H$_2$), 2.01 (4 H, apparent br d, separation 4.5 Hz, —CH$_2$CH=CHCH$_2$—), 2.61 (1 H, br s, 3-H), 2.80 (1 H, br t, J 4 Hz, 3-H), 3.1.5 (1 H, br s, 2-H), 3.38 (1 H, dd, J 11.5 and 6 Hz, 1-H), 3.45–3.54 (2 H, m, α-H$_2$), 3.69–3.72 (1 H, m, 1-H) and 5.34 (2 H, br s, —CH$_2$CH=CHCH$_2$—).

3-O-Oleyl-rac-glycero-1-phosphate (26)

A mixture of 98% phosphoric acid (0.18 g, 1.9 mol) and oleyl glycidol (25) (0.4 g, 1.2 mmol) in dry CH$_2$Cl$_2$ was refluxed for 16 h. TLC analysis showed the reaction to be complete and the mixture was concentrated to give the title phosphate. (26) (0.501 g, 96%) as a colourless oil.

$^1$H NMR (360 MHz; CDCl$_3$): δ 0.87 (3 H, t J 6.5 Hz, Me), 1.27 (22 H, apparent br d, separation 6 Hz, —(CH$_2$)$_5$— and —(CH$_2$)$_6$—), 1.55 (2 H, br s, β-H$_2$), 1.98–2.03 (4 H, m, —CH$_2$CH=CHCH$_2$—), 3.44–3.51 (4 H, m, 3-H$_2$ and —H$_2$), 3.53–4.12 (3 H, m, 2-H and 1-H$_2$), 5.30–5.38 (2 H, m, —CH$_2$CH=CHCH$_2$—) and 6.43 (2 H, br s, 2×OH); $^{31}$P NMR (146 MHz; CDCl$_3$): δ 1.68; ESI-MS(m/z, −ve): 421 (M-H$^+$, 100%).

Synthesis of 3-O-Oleyl oxypropyl-1-phosphate (30)
Dimethyl 3-oleyloxypropyl-1-phosphate (29)

To a suspension of NaH (1.98 g, 13.1 mmol) and anhydrous NaI (0.40 g, 13.4 mmol) in dry DMF (30 mL) under N$_2$ was added dropwise 1,3-propanediol (0.95 mL, 13.1 mmol) over a 30 min period. Next, oleyl tosylate (13) (5.6 g, 13.1 mmol) was added and stirring was continued for 16 h at 50° C. The reaction mixture was quenched with water (50 mL) and extracted with diethyl ether (2×100 mL). The combined organic phases were dried (MgSO$_4$) and concentrated to give crude alcohol 28.

To a solution of 28 (0.51 g, 1.6 mmol) in dry CH$_2$Cl$_2$ (10 mL) was added N-methylimidazole (0.28 mL, 3.5 mmol) followed by the addition of dimethyl chlorophosphate (0.2 mL, 1.9 mmol). After 16 h, the reaction was quenched with sat. KHSO$_4$ (20 mL) and extracted with ethyl acetate (3×50 mL). The organic phases were washed with sat. NaCl (40 mL), dried (MgSO$_4$) and concentrated to give protected phosphate 29 as a yellow oil.

$^1$H NMR (360 MHz; CDCl$_3$): δ 0.88 (3 H, t J 7 Hz, Me), 1.27 (22 H, apparent br d, separation 12 Hz, —(CH$_2$)$_5$— and —(CH$_2$)$_6$—), 1.55–1.57 (2 H, m, β-H$_2$), 1.95–2.01 (6 H, m, —CH$_2$CH=CHCH$_2$— and 2-H$_2$), 3.41–3.43 (2 H, t, J 6 Hz, α-H$_2$), 3.57 (2 H, t, J 6.5 Hz, 3-H$_2$), 3.77 and 3.80 (each 3 H, s, 2×OMe), 4.20 (2 H, m, 1-H$_2$) and 5.33–5.38 (2 H, m, —CH$_2$CH=CHCH$_2$—); ESI-MS (m/z, +ve): 435 (MH$^+$, 100%).

3-O-Oleyloxypropyl-1-phosphate (30)

To a solution of dimethyl phosphate 29 (0.26 g, 0.59 mmol) in dry CH$_2$Cl$_2$ (8 mL) was added BSA (0.30 mL, 1.2 mmol) followed by the addition of TMSBr (0.24 mmol). After 15 min, TLC analysis showed complete consumption of the starting material and the reaction was quenched with 1/1 MeOH/H$_2$O (2 mL, v/v) for 15 min, followed by the addition of sat. KHSO$_4$ (5 mL). The reaction mixture was subsequently extracted with ethyl acetate (2×30 mL), the organic extracts were combined, dried (MgSO$_4$) and concentrated to give the title phosphate (30) as an oil.

$^1$H NMR (360 MHz; CDCl$_3$): δ 0.88 (3 H, t, J 7 Hz, Me), 1.27 (22 H, apparent br d, separation 6 Hz, —(CH$_2$)$_5$— and —(CH$_2$)$_6$—), 1.56 (2 H, br s, β-H$_2$), 1.95–2.01 (6 H, m, 2-H$_2$ and —CH$_2$=CHCH$_2$—), 3.43 (2 H, t, J 6 Hz, α-H$_2$), 3.57 (2 H, br s, 3-H$_2$), 4.12 (2 H, br s, 1-H$_2$), 5.33–5.38 (2 H, m, —CH$_2$CH=CHCH$_2$—) and 8.06 (2 H, br s, 2×OH); $^{31}$P NMR (146 MHz; CDCl$_3$): 1.95; ESI-MS (m/z, −ve): 405 (M-H$^+$, 100%).

Synthesis of 3-O-Oleyl-2-O-methyl-rac-glycero-1-phosphate (36)
Dimethyl 1-O-oleyl-2-O-methyl-rac-glycero-3-phosphate (35)

To a solution of tosyl chloride (19.1 g, 0.10 mol) in dry CH$_2$Cl$_2$ (200 mL) at 0° C. was added TEA (15.3 mL, 0.10 mol) and oleyl alcohol (37.2 mL, 0.10 mol). The reaction mixture was allowed to warm to 20° C. and was subsequently stirred for 3 days. Next, the solvent was removed in vacuo and the resulting residue was redissolved in ethyl acetate (400 mL), washed with sat. NaHCO$_3$ (40 mL), dried (MgSO$_4$), concentrated and subjected to silica-gel column chromatography [eluent: hexane/CH$_2$Cl$_2$, 66:33, v/v] to give oleyl tosylate (34) as an oil.

To a mixture of NaH (4.8 g, 120 mmol) and NaI (0.2 g) in dry DMF (20 mL) was added solketal (5.0 mL, 40 mmol) dropwise over a 30 min period. Once the effervescence had stopped, oleyl tosylate (34) (16.9 g, 40 mmol) was added and the reaction mixture was left for 3 days at 50° C. Then, H$_2$O (10 mL) was added and the mixture was extracted with diethyl ether (2×100 mL), the combined organic phases were dried (MgSO$_4$) and evaporated to dryness. The residue was taken up in THF (150 mL), 2M HCl was added until the solution turned turbid and the reaction was left to stir for 16 h. The mixture was concentrated and subjected to silica-gel column chromatography [eluent: ethyl acetate/hexane, 50/50, v/v] to give 1-O-oleyl-rac-glycerol (32) as an oil. Diol 32 (2.0 g, 5.97 mmol) was added dropwise to a solution of trityl chloride (1.66 g, 6.0 mmol) in anhydrous pyridine (10 mL). The reaction was left to stir for 16 h after which the solvent was removed by co-evaporation with toluene (2×5 mL). Then, part of the residue (1.0 g, 1.7 mmol) was added dropwise to a suspension of NaH (0.14 g, 3.4 mmol) in THF (50 mL), followed by the addition of MeI (0.22 mL, 3.4 mmol). After 16 h, TLC analysis showed that the reaction had gone to completion and H$_2$O (5 mL) was added followed by concentration of the reaction mixture. The residue was partitioned between H$_2$O (20 mL) and diethyl ether (100 mL), the organic extract was washed with sat. NaHCO$_3$ (10 mL), dried (MgSO$_4$) and concentrated to give 1-O-oleyl-2-O-methyl-3-O-trityl glycerol (33) as an oil.

Crude 33 (1.16 g) was dissolved in CH$_2$Cl$_2$ (10 mL) after which trifluoroacetic acid (2 mL) was added. The reaction mixture was stirred for 5 min and excess TFA was quenched by adding solid NaHCO$_3$ until effervescence ceased. The mixture was diluted with H$_2$O (10 mL), extracted with CH$_2$Cl$_2$ (2×50 mL) and the combined organic phases were dried (MgSO$_4$), concentrated and subjected to silica-gel column chromatography [eluent: hexane/ethyl acetate, 80/20, v/v] to give glycerol derivative 34 (0.28 g, 42%,) as an oil.

$^1$H NMR (360 MHz; CDCl$_3$): δ 0.88 (3 H, t J 7 Hz, Me), 1.27 (22 H, apparent br d, separation 9.5 Hz, —(CH$_2$)$_5$— and —(CH$_2$)$_6$—), 1.53–1.60 (2 H, m, α-H$_2$), 1.98–2.01 (4 H, m, —CH$_2$CH═CHCH$_2$—), 3.37–3.46 (3 H, m, 2-H and α-H$_2$), 3.47 (3 H, s, OMe), 3.52 (1 H, dd, J 10 and 5 Hz, 1-H), 3.56 (1 H, dd, J 10 and 5 Hz, 1-H), 3.65 (1 H, dd, J 11.5 and 5.5 Hz, 3-H), 3.76 (1 H, dd, J 11.5 and 4 Hz, 3-H) and 5.30–5.39 (2 H, m, —CH$_2$CH═CHCH$_2$—).

To a solution of compound 34 (0.26 g, 0.76 mmol) in dry CH$_2$Cl$_2$ (8 mL) was added N-methylimidazole (67 µl, 0.84 mmol) followed by the addition of dimethyl chlorophosphate (0.12 mL, 1.22 mmol). After 1 h, TLC analysis showed the reaction to be complete, sat. KHSO$_4$ (20 mL) was added and the mixture was extracted with ethyl acetate (3×50 mL). The organic phases were combined and washed with sat. NaCl (40 mL), dried (MgSO$_4$), concentrated and subjected to silica-gel column chromatography [eluent: ethyl acetate/ hexanes, 50/50, v/v] to give the title dimethyl phosphate (35) as an oil.

$^1$H NMR (360 MHz; CDCl$_3$): δ 0.88 (3 H, t J 7 Hz, Me), 1.27 (22 H, apparent br d, separation 12 Hz, —(CH$_2$)$_5$— and —(CH$_2$)$_6$—), 1.54–1.59 (2 H, m, β-H$_2$), 1.98–2.01 (4 H, m, —CH$_2$CH═CHCH$_2$—), 3.41–3.56 (5 H, m, 2-H, 3-H$_2$ and α-H$_2$), 3.47 (3 H, s, OMe), 3.77 (3 H, d, J 2 Hz, OMe), 3.80 (3 H, d, J 2 Hz, OMe), 4.08 (1 H, ddd, J 11, 7.0 and 5.5 Hz, 1-H), 4.19 (1 H, ddd, J 11, 7.0 and 4 Hz, 1-H) and 5.30–5.39 (2 H, m, —CH$_2$CH═CHCH$_2$—); $^{31}$P NMR (146 MHz; CDCl$_3$): 2.60; ESI-MS (m/z, +ve): 465 (MH$^+$, 100%).

3-O-Oleyl-2-O-methyl-rac-glycero-1-phosphate (36)

To a stirring solution of protected phosphate 35 (85 mg, 0.18 mmol) in dry CH$_2$Cl$_2$ (5 mL) was added BSA (140 µL, 0.55 mmol) and TMSBr (50 µL, 0.05 mmol). After 30 min, TLC analysis showed the reaction to be complete, 1/1 MeOH/H$_2$O (1 mL, v/v) was added and left for 30 min. Then, sat. KHSO$_4$ (5 mL) was added and the mixture was extracted with ethyl acetate (2×30 mL), the combined organic extracts were dried (MgSO$_4$), evaporated to dryness and subjected to Sephadex LH-20 column chromatography [eluent: MeOH/CH$_2$Cl$_2$, 50/50, v/v] to give phosphate 36 as an oil.

$^1$H NMR (360 MHz; CDCl$_3$): δ 0.87 (3 H, t J 7 Hz, Me), 1.25 (22 H, apparent br d, separation 4 Hz, —(CH$_2$)$_5$— and —(CH$_2$)$_6$—), 1.55–1.56 (2 H, m, β-H$_2$), 1.98–2.03 (4 H, m, —CH$_2$CH═CHCH$_2$—), 3.40–3.58 (5 H, m, 2-H, 3-H$_2$ and α-H$_2$), 3.46 (3 H, s, OMe), 3.99–4.05 (2 H, m, 1-H$_2$), 5.30–5.37 (2 H, m, —CH$_2$CH═CHCH$_2$—) and 5.75 (2 H, br s, 2×OH); $^{31}$P NMR (146 MHz, CDCl$_3$): 1.68; ESI-MS (m/z, −ve): 435 (M-H$^+$, 100%).

LacZ assays in response to lysophosphatidic acid and LPA analogs- JEY5+pJE15 was grown on SC media containing either 2% galactose or 2% glucose lacking uracil to an approximate O.D. of 0.1–0.5 prior to the addition of lipid or α-factor. Acyl-LPA chain length analogs; 6:0, 10:0, 14:0, 16:0, 18:0, 18:1 and 24:1 (Avanti Polar Lipids) were stored dissolved in chloroform and dried down under vacuum immediately prior to experiments and resuspended in BBS/ EDTA (50 mM NH$_4$HCO$_3$, 104 mM NaCl, 250 µM EDTA2Na pH 7.63) at 20 mM with sonication until the solution was clear. The other analogs that were custom synthesized for this report were stored in 100% ethanol at −20° C., dried and resuspended in BBS/EDTA immediately prior to use. Analogs not having a phosphate were stored in 100% DMSO and added directly to the yeast culture. Final DMSO concentration did not exceed 0.4%. Cells were grown for 7 hours prior to assaying at which time 100 µl of yeast culture were then added to 9001 assay buffer (60 mM Na2HPO$_4$, 40 mM NaH$_2$PO$_4$, 10 mM KCl, 0.1 mM MgSO$_4$, pH 7.0 plus 2.7 mL β-mercaptoethanol per liter) plus 50 µl 0.1% SDS+three drops Chloroform. Cells were vortexed for 10 seconds and incubated for 5 minutes at 28° C. 200 µl of 4mg/ml o-nitrophenol-β-D-galactopyranoside (ONPG, Sigma) was added and the reaction was incubated 30 minutes at 28° C. The assay was stopped by the addition of 500 µl 1M Na$_2$CO$_3$. Color development was measured at A$_{420}$ and normalized to A$_{600}$. Units were expressed as Miller Units. Competition assays between 18:1 acyl-LPA and the short chain analogs were essentially performed in the same manner except that both lipids were added simultaneously and the yeast was allowed to grow for the standard seven-hour time period. ERK immune complex kinase assays- C3H/10T½ cells were cultured in Basal Medium Eagle (BME, Gibco)+10% heat inactivated fetal calf serum until quiescent in 6 cm dishes. Cultures were serum starved for 18 hours in BME and stimulated with LPA or an LPA analog for 5 minutes. Dishes were placed on ice, washed with ice cold PBS and lysed in 500 µL lysis buffer (20 mM Tris pH8.0, 137 mM NaCl, 1mM EGTA, 1% Triton X-100, 10% glycerol, 15 mM MgCl$_2$, 1 mM NaVO$_4$, 50 mM NaF, 1mM Pefabloc, 20 µM Leupeptin, 10 µg/mL Aprotinin). To 200 µg total protein, 2 µL anti-ERK1 and 2 µL anti-ERK2 (Santa Cruz) plus 20 µL protein G-agarose beads (Boehringer-Mannheim, 50% slurry) were added and incubated with continuous rocking for two hours at 4° C. The agarose bead-ERK immune complexes were washed twice with 1mL lysis buffer then once in 1mL kinase buffer (30 mM Tris pH 8.0, 20 mM MgCl$_2$, 2 mM MnCl$_2$) and then drained to dryness with a fine gauge Hamilton syringe. The kinase reaction was started by adding 30 µL kinase buffer containing 2 µg myelin basic protein (MBP, Sigma), 10 µM cold ATP and 2.5 µCi [$^{32}$P]γ-ATP (Amersham). The reaction was incubated for 25 minutes at 30° C. and then stopped by the addition of 10 µL hot 4×-sample buffer. The phosphorylated MBP was resolved on a 14% SDS-PAGE gel (Novex), stained, dried and the Coomassie Brilliant Blue-stained band was excise and counted on a liquid scintillation counter (Beckman).

I claim:

1. A method of activating an Edg2 receptor on the surface of a cell, the method comprising exposing the cell to an Edg2 receptor activating amount of a compound of the formula:

wherein, X is selected from the group consisting of hydroxyl,

Z is selected from the group consisting of hydrogen, bromine, chlorine, fluorine, iodine, and $OR_2$, wherein $R_2$ is an unsaturated alkyl containing 1–3 carbons; and $R_1$ is a saturated or unsaturated alkyl chain containing 15–17 carbons.

2. The method of claim 1 wherein X is phosphate.

3. The method of claim 1 wherein $R_1$ is a saturated or unsaturated alkyl chain containing 17 carbons.

4. The method of claim 1 wherein Z is selected from the group consisting of hydrogen, bromine, and oxymethyl.

5. The method of claim 1 wherein the compound is 1-(3-propyl oleoate) phosphate.

6. The method of claim 1 wherein the compound is 3-O-oleoyl-2-O-methyl-rac-glycero-1-phosphate.

7. The method of claim 1 wherein the compound is 1-O-oleoyl-2-O-methyl-rac-glycerol.

8. The method of claim 1 wherein the compound is 3-O-oleoyl-2-deoxy-2-bromo-rac-glycero-1-phosphate.

9. The method of claim 1 wherein the compound is 1-O-oleoyl-2-deoxy-2-bromo-rac-glycerol.

10. The method of claim 1 wherein the cell is a yeast cell.

11. The method of claim 1 wherein the cell is a mammalian cell.

* * * * *